United States Patent [19]

Kamide et al.

[11] Patent Number: 4,579,943

[45] Date of Patent: Apr. 1, 1986

[54] CELLULOSE DERIVATIVE EXCELLENT IN LIQUID ABSORBING PROPERTY, PROCESS FOR PREPARING SAME AND STRUCTURE CONTAINING SAME

[75] Inventors: Kenji Kamide, Ikoma; Kunihiko Okajima, Takatsuki, both of Japan

[73] Assignee: Asahi Kasei Kogyo Kabushiki Kaisha, Osaka, Japan

[21] Appl. No.: 666,445

[22] Filed: Oct. 30, 1984

[30] Foreign Application Priority Data

Oct. 31, 1983 [JP] Japan ................. 58-202703

[51] Int. Cl.$^4$ ............................................. C08B 15/04
[52] U.S. Cl. ..................... 536/98; 428/274; 428/532
[58] Field of Search .................... 536/97, 98, 57; 428/274, 532

[56] References Cited

U.S. PATENT DOCUMENTS

| | | | |
|---|---|---|---|
| 2,816,889 | 12/1957 | Branan | 536/97 |
| 3,055,369 | 9/1962 | Graham | 536/97 |
| 3,375,245 | 3/1968 | Dearborn | 536/98 |
| 3,723,413 | 3/1973 | Chatterjee et al. | 536/97 |
| 3,918,899 | 11/1975 | Perrier et al. | 536/98 |
| 4,009,319 | 2/1977 | Cline | 428/532 |
| 4,333,464 | 6/1982 | Nakano | 428/532 |
| 4,340,731 | 7/1982 | Colombo et al. | 536/98 |
| 4,377,648 | 3/1983 | Menault et al. | 428/532 |

*Primary Examiner*—Ronald W. Griffin
*Attorney, Agent, or Firm*—Finnegan, Henderson, Farabow, Garrett & Dunner

[57] ABSTRACT

Disclosed is carboxymethyl cellulose or its salt derived from cellulose having a crystal form of cellulose II, wherein the total saturation degree $<<F>>$ represented by the following formula:

$$<<F>> = <<f_2>> + <<f_3>> + <<f_6>>$$

wherein $<<f_2>>$, $<<f_3>>$ and $<<f_6>>$ represent the probabilities of substitution of substituent groups for OH groups located at the $C_2$, $C_3$ and $C_6$ positions, respectively, of the glucose ring constituting the cellulose, is in the range of from 0.10 to 0.64. This carboxymethyl cellulose or its salt is excellent in liquid absorbing property and is prepared by treating cellulose having a crystal form of cellulose II with an alkali and then reacting the treated cellulose with monochloroacetic acid or sodium monochloroacetate. This carboxymethyl cellulose or its salt can be used in the form of a structure such as a sheet, a woven fabric or a nonwoven fabric.

9 Claims, 10 Drawing Figures

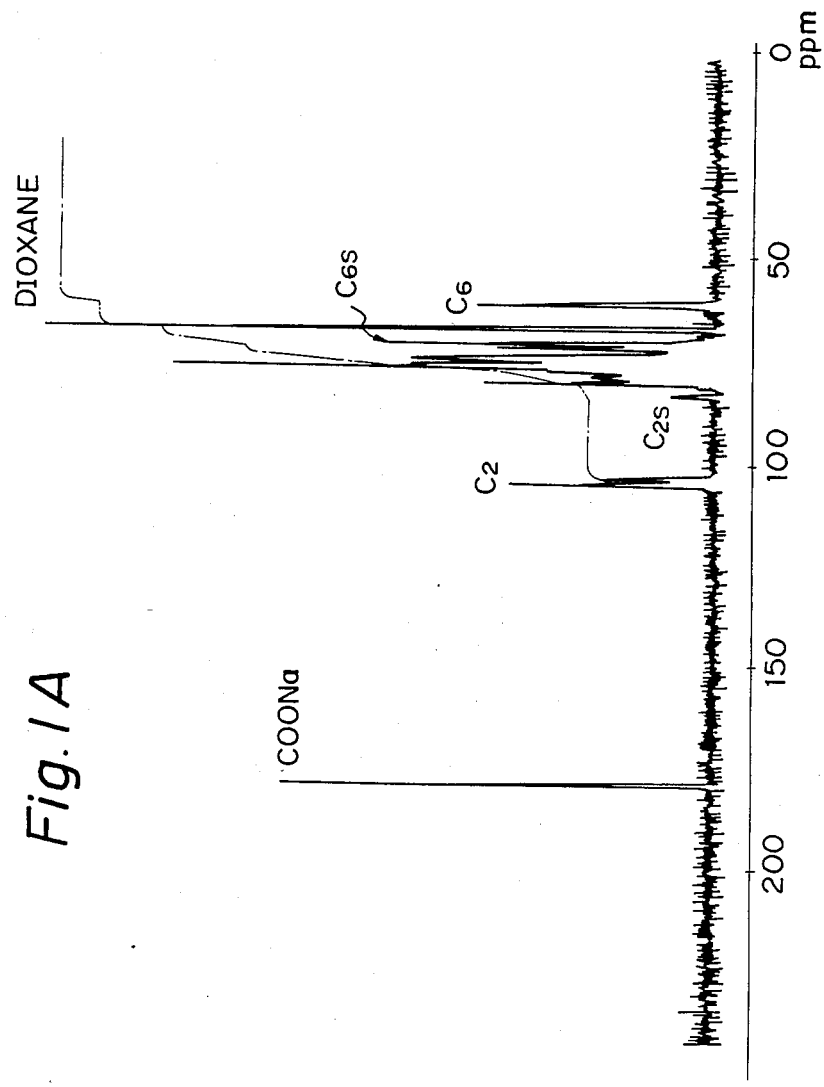

CELLULOSE DERIVATIVE EXCELLENT IN LIQUID ABSORBING PROPERTY, PROCESS FOR PREPARING SAME AND STRUCTURE CONTAINING SAME

BACKGROUND OF THE INVENTION (1) Field of the Invention

The present invention relates to novel carboxymethyl cellulose (carboxymethyl cellulose will be hereinafter referred to as "CMC" for brevity), and a process for the preparation thereof. Furthermore, the present invention relates to a CMC structure excellent in processability and handling property, which is prepared from this novel CMC.

(2) Description of the Prior Art

Ordinary available CMC is prepared from natural cellulose (cellulose having a crystal form of cellulose I) such as linter or pulp as the starting material. Up until now, regenerated cellulose (cellulose having a crystal form of cellulose II) has not been used for the starting material of ordinary available CMC. There are two reasons for this. First, CMC can be easily prepared from natural pulp or linter. (Natural pulp or linter is prepared by removing foreign substances from a crude material such as wood or cotton linter and is available at reasonable cost.) It is therefore unreasonable economically to use, as the starting material, cellulose II obtained by further processing such natural cellulose. Second, there can be mentioned the state of the cellulose industry which has been established based on empirical facts and therefore there is a low level of understanding of the nature of cellulose chemistry or science. For example, the technique of mercerization (alkali cellulose formation) was already known in the 1870's. While it has been applied to modification of cotton fabrics for imparting silk-like luster to them, however, it has not been applied to modification of regenerated cellulose fibers. Yet regenerated cellulose fibers were already developed and marketed about 30 years after the establishment of the mercerization technique. The reason for this is that regenerated cellulose fibers are already similar to natural silk fibers, it was so true that application of mercerization was not considered necessary. In cellulose industry, it was only about 10 years ago that the fact the structure of alkali cellulose from cellulose I is different from the structure of alkali cellulose from cellulose II was accepted. Therefore, the cellulose industry does not have the scientific expertise for discriminating the differences in properties among cellulose derivatives obtained by the heterogeneous reaction from cellulose I and cellulose II, through alkali celluloses.

Most of ordinary available CMC has a total degree of substitution (hereinafter referred to as "$<<F>>$" for brevity) of the water-soluble region. Only CMC used as an ion exchange resin has a $<<F>>$ of the water-insoluble region. A bench-scale method in which cellulose in the form of a fabric is converted to CMC to improve dyeability has been reported, but this research is directed to cotton alone. No literature proposes application of this method to regenerated cellulose.

The processes for preparing CMC from natural cellulose can be roughly divided into a water medium method and a solvent medium method. These methods are characterized in that in order to increase the permeability of reactants, natural cellulose is converted to alkali cellulose and then the alkali cellulose is reacted with monochloroacetic acid or sodium monochloroacetate. Furthermore, in order to control occurrence of a side reaction by monochloroacetic acid or sodium monochloroacetate, such means as mechanical pulverization, compression, shearing or stirring is customarily adopted so as to sufficiently mix starting cellulose with a reactant solution. Accordingly, CMC is obtained ordinarily in the form of a powder or ultra-fine fiber. Since CMC is ordinarily used in fields where the emulsion stabilizing effect or thickening effect is utilized, CMC is used ordinarily in the powdery form. It is pointed out that the probability of substitution at the $C_2$ position in the glucose ring of commercial CMC is very large see, for example, Alain Parfondry et al, Carbohydrate Research, 57 (1977), 39–40 .

Since three substitutable OH groups (at $C_2$, $C_3$ and $C_6$ positions) are present in the glucose ring of cellulose, it is obvious that properties of cellulose vary depending upon the probability of substitution [$<<f_k>>$(k=2, 3, 6)] at the respective positions. This $<<f_k>>$ naturally differs according to the method for the preparation of a cellulose derivative and the kind of the starting cellulose used. Moreover, the difference of the starting cellulose results in not only a difference of $<<f_k>>$ but also a difference of the internal structure. Accordingly, there is a possibility that commercial cellulose derivatives called by general names such as CMC, methyl cellulose, ethyl cellulose, cellulose acetate, cellulose acetate butyrate, cellulose nitrate, hydroxypropyl cellulose, hydroxyethyl cellulose and ethylhydroxyethyl cellulose will be converted to derivatives having novel structures and properties.

SUMMARY OF THE INVENTION

It is the primary object of the present invention to provide CMC or its salt having a surprisingly high liquid absorbing property, which is derived from cellulose having a crystal form of cellulose II (regenerated cellulose).

More specifically, in accordance with the present invention, there is provided CMC or its salt derived from cellulose having a crystal form of cellulose II, wherein the total substitution degree $<<F>>$ of the carboxylmethyl cellulose or its salt represented by the following formula:

$<<F>>=<<f_2>>+<<f_3>>+<<f_6>>$ wherein $<<f_2>>$, $<<f_3>>$ and $<<f_6>>$ represent the probabilities of substitution of substituent groups for OH groups located at the $C_2$, $C_3$ and $C_6$ positions, respectively, of the glucose ring constituting the cellulose, is in the range of from 0.10 to 0.64.

This CMC and its salt can be prepared by treating cellulose having a crystal form of cellulose II with an alkali and reacting the alkali-treated cellulose with monochloroacetic acid or sodium monochloroacetate.

This CMC or its salt can be utilized for a sheet-like structure, a woven fabric structure or a nonwoven fabric structure comprising this CMC or its salt as one constituent.

BRIEF DESCRIPTION OF THE DRAWINGS

FIG. 1A and FIG. 1B show $^{13}$C-NMR (107.5 MHz) spectra of CMC of the present invention and comparative CMC, in which the numbers on the spectra indicate the positions of carbons constituting the glucose ring of CMC and symbol S indicates that OH at the position of the corresponding carbon atom is carboxymethylated.

I a): starting cellulose I (comparison)
I (b): CMC (comparison) obtained from cellulose I
II (a): starting cellulose II
II (b): CMC (present invention) obtained from cellulose II In FIG. 2, the numeral represents the diffraction angle $2\theta$ of the peak indicated by the arrow.

Figure 3:
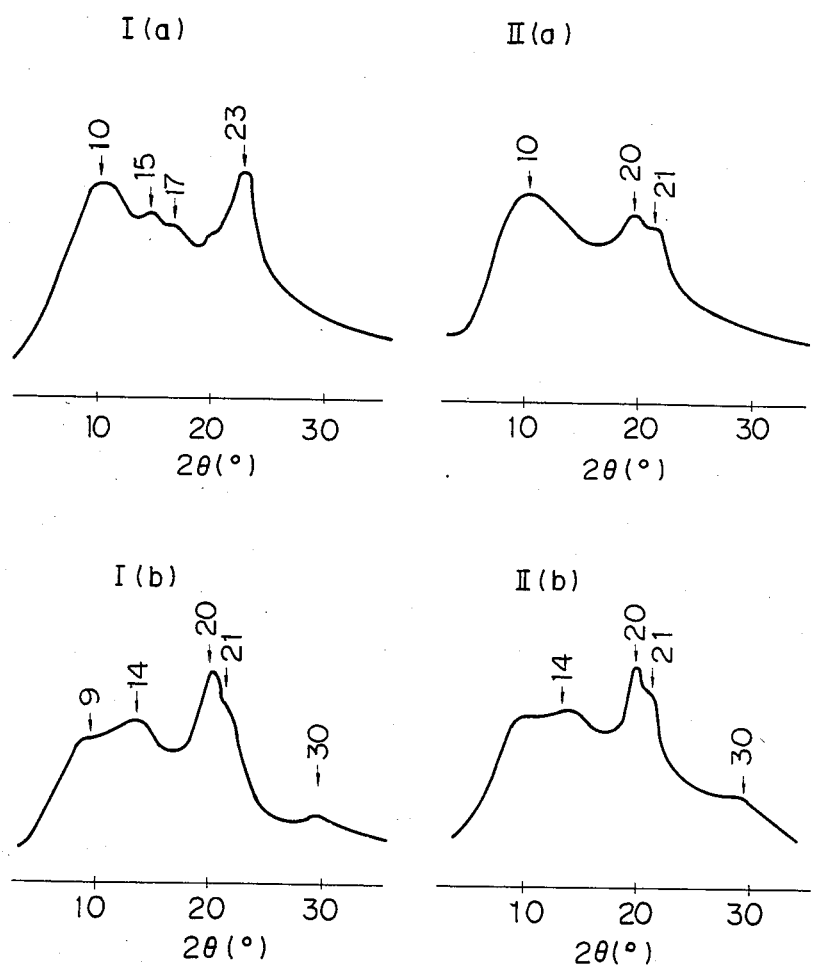

FIG. 3 shows X-ray diffraction patterns of the following substances.

I (a): cellulose I/alkali mixture (comparison) obtained according to a method similar to the method of the present invention
I(b): alkali cellulose I—I (comparison) obtained according to the conventional method
II(a): cellulose II/alkali mixture obtained according to the method of the present invention
II(b): alkali cellulose I-II (comparison) obtained according to the conventional method

DETAILED DESCRIPTION OF THE PREFERRED EMBODIMENTS

The sodium salt of the CMC of the present invention has a capacity of absorbing pure water in an amount at least 20 times its own weight. The amount of pure water absorbed can be up to about 100 times its own weight. By the term "its own weight" is meant the weight of CMC or its salt which has been dried at 60° C. for 8 hours and allowed to stand still for 24 hours in an atmosphere maintained at a temperature of 18° C. and a relative humidity of 60%.

Even with CMC and its salt derived from cellulose having a crystal form of cellulose II, the desired liquid absorbing property cannot be attained if the value $<<F>>$ is smaller than 0.10. Furthermore, if the value $<<F>>$ is larger than 0.64, the desired liquid absorbing property is not attained and the amount of the portion of CMC or its salt which is dissolved out by water is increased. Thus, a practical adsorbing material or liquid absorbing material cannot be provided.

Regenerated cellulose is ordinarily cellulose having a crystal form of cellulose II, and regenerated cellulose is obtained by converting natural cellulose to alkali cellulose and regenerating the cellulose under appropriate conditions or by dissolving natural cellulose in a solvent and regenerating the cellulose. From the industrial viewpoint, a cellulose xanthate solution (viscose) and a cellulose/cuprammonium solution are preferred as the cellulose solution to be subjected to regeneration. Solutions that can be used in the present invention are not limited to these solutions. Cellulose/inorganic acid solutions, cellulose/aqueous inorganic salt solutions, and solutions of cellulose in recently found cellulose solvents such as dimethylsulfoxide/paraformaldehyde, organic solvents/dinitrogen tetraoxide, dimethylformamide/chloral, sulfur dioxide/amines, N-methylmorpholine-N-oxide, N-ethylpyridium chloride/organic solvents, N,N-dimethylacetamide/lithium chloride, liquid ammonia/thiocyanate and dimethylsulfoxide/carbon disulfide/amines can also be used. In principle, a solution of a derivative that can easily be regenerated to cellulose, for example, cellulose acetate, can also be used. An acid or alkali can be used for regeneration of cellulose from a cellulose solution such as mentioned above.

The regenerated cellulose obtained in the abovementioned manner has a very high purity, and can be advantageously used for formation of the cellulose derivative of the present invention. When $<<F>>$ is smaller than about 0.65, the CMC tends to retain the X-ray diffractometric crystal form of the starting material (see FIG. 2). Accordingly, as described hereinafter, the structure, that is, the state of molecular packing, of CMC of the present invention (hereinafter referred to as "CMC II") derived from regenerated cellulose (i.e., cellulose having a crystal form of cellulose II) is different from the structure of CMC (hereinafter referred to as "CMC I") derived from natural cellulose (i.e., cellulose having a crystal form of cellulose I). This difference results in a great difference of the liquid absorbing property. Supposing that the amount of water absorbed when CMC is dipped in pure water at 37° C. for 10 minutes is a function of $<<F>>$, the range of $<<F>>$ capable of absorbing water in an amount at least 40 times its own weight is from 0.30 to 0.60 in case of CMC I and from 0.15 to 0.40 in case of CMC II. Thus, CMC II shows a moisture absorbing property at a much smaller value $<<F>>$ than in case of CMC I. Accordingly, CMC II is excellent in the property of retaining its state and dimension after absorption of moisture (ordinarily, the gel state), making CMC II advantageous in practical use. This excellent dimensional stability results from the excellent liquid retaining property after absorption of a liquid.

CMC II of the present invention is prepared by using cellulose having a crystal form of cellulose II (regenerated cellulose) as the starting material and treating it according to a method similar to the known carboxymethylation method. Namely, cellulose having a crystal form of cellulose II is treated with an alkali and the alkali-treated cellulose is reacted with monochloroacetic acid or sodium monochloroacetate. According to this method, the starting cellulose having a crystal form of cellulose II is converted to alkali cellulose I-II by the alkali treatment, which alkali cellulose has a crystal form different from the crystal form of alkali cellulose derived from natural cellulose. The form of the starting cellulose is not particularly critical. The starting cellulose may be in the form of a powder, a fiber, a fabric or a nonwoven fabric.

The CMC of the present invention can be obtained usually in the form of a free acid or a sodium salt, and can be converted to various salts. For example, the CMC of the present invention can be converted to salts of alkali metals such as potassium and lithium, alkaline earth metals such as calcium and magnesium, amphoteric metals such as aluminum, transition metals such as titanium, zirconium, chromium and mercury, and lead. Ordinarily, a divalent or polyvalent metal reduces the liquid absorbing property of the CMC. Therefore, a salt of a divalent or polyvalent metal is not preferred when a high liquid absorbing property is desired. However, when it is necessary to adjust the liquid absorbing property, the species of the metal as well as the substitution degree are important. Moreover, each of metals forming salts with CMC can impart peculiar characteristics to the CMC in addition to the liquid absorbing property. For example, it is expected that the mercury salt will exert a fungicidal effect and a lead salt will exert a hemostatic effect. Since the intended liquid absorbing property of the present invention is mainly a property of absorbing an aqueous solution, the sodium salt is most preferred among various metal salts.

If a specific preparation process is adopted for the production of the CMC of the present invention, CMC II especially excellent in the property of absorbing a physiological saline solution can be obtained. This CMC II is characterized in that the sum of substitution possibilities of carboxymethyl groups at the $C_2$, $C_3$ and $C_6$ positions $<<F>>(=<<f_2>>+<<f_3>>+<<f_6>>)$ is in the range of from 0.10 to 0.64 as pointed out hereinbefore, the requirement of $<<f_6>> > <<f_2>>$ and $<<f_6>> > <<f_3>>$ is satisfied, that is, the possibility of substitution at the $C_6$ position is highest, and the $<<f_6>>/(<<f_2>>+<<f_3>>)$ ratio is at least 1.5. The value of $<<F_6>>/(<<f_2>>+<<f_3>>)$ mentioned here is determined according to the following procedures. Namely, sample CMC is dissolved at a concentration of about 3% by weight in a 5% by weight solution of NaOH in $D_2O$. Measurement is carried out on this solution at 60° C. by using 100.7 MHz $^{13}$C-NMR (Pulse-Fourier transform type) under conditions of 90° pulses, a repetition time of 2 seconds and 5000 times integration. The value is obtained by performing calculation based on the obtained measurement data according to the following equations:

$$<<F>> = \frac{CO^*}{C_1} \text{ or } \frac{C_{4s}}{C_4 + C_{4s}} \quad (1)$$

$$<<f_6>> = \frac{C_{6s}}{C_6 + C_{6s}} \quad (2)$$

$$<<f_2>> + <<f_3>> = \quad (3)$$
$$\frac{3 \times (C_4 + C_{4s}) - (C_2 + C_3 + C_5 + C_{5s})}{(C_4 + C_{4s})}$$

In the above equations, S represents a peak caused to appear because of introduction of a substituent at the corresponding position or because of introduction of a substituent into any of the $C_2$, $C_3$ and $C_6$ positions. In the right terms of the equations (1) through (3), all symbols express the peak intensity. *CO represents a carbonyl carbon peak of the carboxymethyl group. Although two peaks appear in the vicinity of $C_{6s}$ (71 ppm), the peak on the high magnetic field side is designated as the peak of $C_{6s}$ and the peak on the low magnetic field side is designated as the peak of the star carbon of the substituent $-C^*H_2COOH$. Results of the presumption of the NMR peak positions in the respective substitution types are shown in Table 1.

TABLE 1

| Type of CMC | Calculation of Chemical Shift of CMC |  |  |  |  |  |
|---|---|---|---|---|---|---|
|  | Chemical Shift (ppm) | | | | | |
|  | $C_1$ | $C_2$ | $C_3$ | $C_4$ | $C_5$ | $C_6$ |
| Unsubstituted | 104.7 | 75.0 | 76.4 | 80.0 | 76.4 | 61.9 |
| 2-Substituted | 104.3 | 83.9 | 75.2 | 79.6 | 76.1 | 61.4 |
| 3-Substituted | 104.3 | 74.1 | 84.3 | 79.2 | 75.7 | 61.1 |
| 6-Substituted | 104.4 | 74.3 | 75.6 | 78.9 | 74.6 | 70.0 (72.3) |
| 2,3-Substituted | 103.9 | 83.0 | 85.3 | 78.8 | 75.5 | 60.6 |
| 2,6-Substituted | 104.0 | 83.1 | 74.4 | 78.5 | 74.3 | 69.5 (71.8) |
| 3,6-Substituted | 104.0 | 73.4 | 84.7 | 78.1 | 73.9 | 69.2 (71.5) |
| 2,3,6-Substituted | 103.6 | 82.3 | 83.5 | 77.7 | 73.6 | 68.7 (70.0) |

Note
1 Each value is calculated from the chemical shift of CM—glucose.
2 $CH_2$ in the substituent group is expected to appear at about 71.2 ppm.
3 COONa in the substituent group is expected to appear at 178.4 and 178.8 ppm.

Figure 1B:
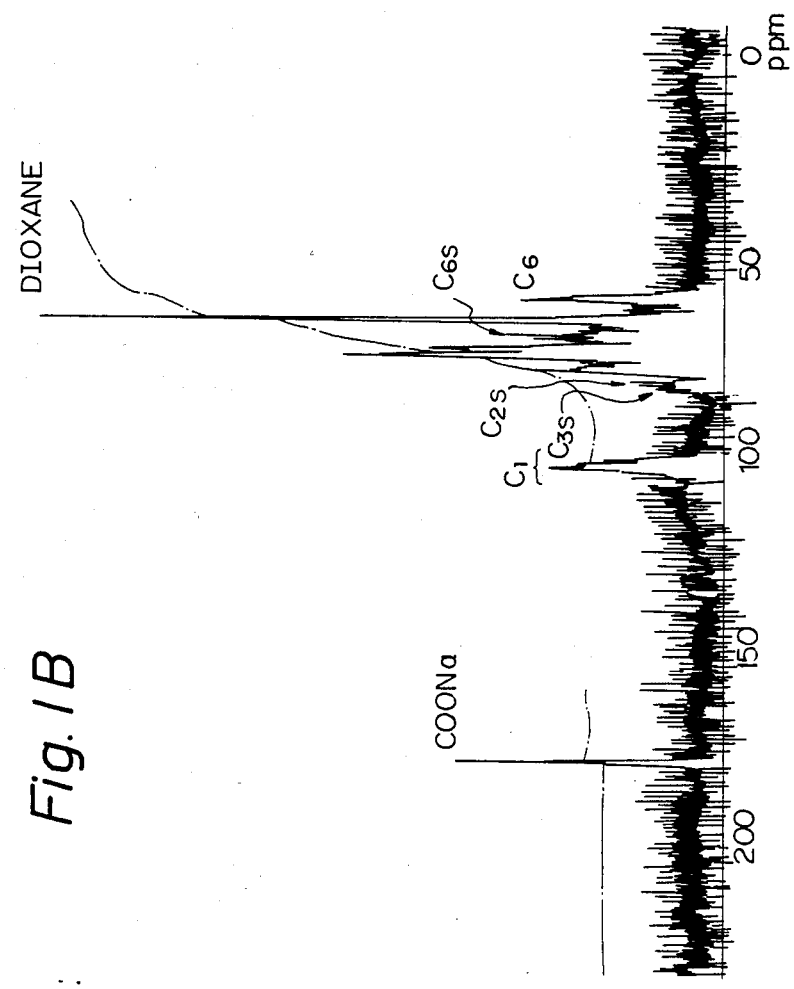

The typical $^{13}$C-NMR spectra (107.5 MHz) of CMC are shown in FIG. 1A and FIG. 1B. From these figures, the difference of CMC II [FIG. 1A] of the present invention from comparative CMC I [FIG. 1B] is apparent. Numbers given in FIG. 1 indicate the positions of carbon atoms forming the glucose ring of CMC. The symbol "s" means that the hydroxyl group attached to the corresponding C position is carboxymethylated. It is readily confirmed that in the CMC of the present invention, the peak of $C_{6s}$ is large, the peak of $C_6$ (unsubstituted) is low and the $<<f_6>>$ value is large. In comparative CMC, peaks attributed to $C_{2s}$ and $C_{3s}$ (at about 83 ppm) are clearly observed, showing that $<<f_6>>$ of CMC of the present invention is considerably higher than that of CMC from natural cellulose.

CMC II of the present invention satisfying the above requirements of $<<F>>$ and $<<f_k>>$ (k=2, 3, 6) is characterized in that the amount absorbed of a physiological saline solution (dipping at 37° C. for 10 minutes) is 20 to 80 times its own weight. In the case of CMC II having an $<<F>>$ value of 0.25 to 0.64, the amount absorbed of a physiological saline solution is at least 25 times its own weight, and can be up to 80 times its own weight. This CMC II is obtained by subjecting regenerated cellulose to an alkali treatment without X-ray-diffractometrically complete conversion to alkali cellulose and carboxymethylating the resulting alkali-treated cellulose. This treatment is to strongly reflect the structure of regenerated cellulose on final CMC. By the term "without X-ray-diffractometrically complete conversion to alkali cellulose" used herein, it is meant that the treated cellulose is a cellulose/alkali mixture which has not completely been converted to alkali cellulose from the X-ray-diffractometric viewpoint and which does not have a peak at 2θ=30° characteristic to alkali cellulose [see FIGS. 3-I(a) and 3-II(a)]. In the case where cellulose II is used as the starting substance, a cellulose/alkali mixture having no peak at 2θ=14° is meant. More specifically speaking, a cellulose/alkali mixture in which when the relative intensities of peaks at 2θ=9° and 2θ=14°, characteristic to alkali cellulose, are compared, there is found a relation of $I_{2θ(9°)} > I_{2θ(14°)}$ is meant. Incidentally, $I_{2θ(9°)}$ and $I_{2θ(14°)}$ represent the relative intensities at 2θ=9° and 2θ=14°, respectively.

In order to obtain preferred CMC and its salt satisfying the above-mentioned requirements of $<<F>>$ and $<<f_k>>$, it is preferred that during the reaction for formation of CMC, the starting cellulose not be subjected to an operation such as mechanical pulverization, compression, shearing or stirring. Accordingly, in the present invention, the starting regenerated cellulose may be subjected to a reaction in the form of a sheet, a woven fabric or a nonwoven fabric. Thus, this method is advantageous in view of the processability and handling property of the final product.

CMC II obtained according to this method has novel characteristics and is different in chemical structure from CMC obtained from natural cellulose by the conventional aqueous medium or solvent medium method and also from CMC obtained when a method similar to the above-mentioned method of the present invention is applied to natural cellulose. In each of these comparative products of CMC, the $<<f_6>>/(<<f_2>>+<<f_3>>)$ ratio is smaller than 1.1. In this point, they are different from the CMC of the present invention. This difference results directly in the difference of the liquid absorbing property. More specifically, in case of CMC obtained by applying a method similar to the method of the present invention to natural cellulose, the $<<F>>$ value is in the range of from 0.12 to 0.70 and the amount of a physiological saline solution absorbed at 37° C. does not exceed 35 times its own weight. On the other hand, in case of the CMC II of the present invention, if the $<<F>>$ value is in the range of from 0.30 to 0.62, the amount of a physiological saline solution absorbed is always at least 35 times its own weight.

The first characteristic feature of the process for preparing CMC II according to the present invention is that as pointed out hereinbefore, regenerated cellulose is treated with an alkaline solution incapable of converting regenerated cellulose X-ray-diffractometrically completely to alkali cellulose. As specific examples of the alkaline solution, there can be mentioned an aqueous solution containing sodium hydroxide at a concentration of, for example, 5 g/dl or less and a water-containing organic solvent solution containing sodium hydroxide, the concentration of sodium hydroxide being not particularly critical. In the case of the latter solution, the concentration of sodium hydroxide is adjusted so that no precipitates of sodium hydroxide are formed. As the organic solvent, there are preferably used methanol, ethanol, isopropanol, benzene and toluene. Conversion of regenerated cellulose to alkali cellulose is influenced by the treatment temperature and treatment time. In order to prevent X-ray-diffractometrically complete conversion to alkali cellulose, the alkali treatment should be conducted at a temperature of 60° C. or less within 30 minutes. The amount of sodium hydroxide is preferably 1 to 4 moles per mole of the glucose residue. The amount of the alkaline solution is not particularly critical, but it is ordinarily preferred that the alkaline solution be used in an amount of 5 to 20 parts by volume per part by weight of regenerated cellulose.

Monochloroacetic acid or sodium monochloroacetate is added directly or in the form of a solution in an appropriate solvent to the regenerated cellulose/alkaline solution mixture obtained by the above treatment, whereby carboxymethylation is effected. The amount of monochloroacetic acid or sodium monochloroacetate may be appropriately determined according to the intended $<<F>>$ value of the final CMC. Water, a halogenated hydrocarbon or an alcohol is used as the solvent for monochloroacetic acid or sodium monochloroacetate. From the viewpoint of the preparation facility, it is preferred that the solvent of the alkaline solution used for the above-mentioned alkaline treatment be used as the solvent for monochloroacetic acid or sodium monochloroacetate. In the process for preparing the CMC II according to the present invention, at the step of adding the reactant (monochloroacetic acid or sodium monochloroacetate), a considerable amount of the free alkali is left in the alkaline solution. Accordingly, if the side reaction of the reactant is neglected, it is possible to prepare the CMC II of the present invention by mixing and reacting regenerated cellulose with a solution formed by adding the reactant directly to the above-mentioned alklaine solution.

Conditions for the reaction of regenerated cellulose treated with the alkaline solution with the reactant can be optionally determined. Ordinarily, however, this reaction is carried out at a temperature of 60° C. or less within 90 minutes. In the case where an organic solvent is used as the solvent for this reaction, swelling of cellulose is limited, though swelling occurs to a considerable extent when an aqueous solvent is used. Accordingly, a method may be adopted in which the organic solvent (reaction liquid) is forced to be circulated for the reaction through a reaction system in which regenerated cellulose is fixed. For example, a method can be adopted in which a sheet, fabric or nonwoven fabric in the form of a roll is inserted in a cylinder of the inner jetting type having jet holes formed on the peripheral wall thereof, the cylinder is immersed in a reaction liquid tank to cause the reaction liquid to flow from the inside of the cylinder to the outside of the cylinder through the jet holes and the reaction liquid in such an excessive amount as cannot be contained in regenerated cellulose is returned to a reaction liquid feed reservoir, whereby the reaction is carried out while circulating the reaction liquid. After completion of the reaction, neutralization, washing and drying are carried out according to customary procedures.

The thus-obtained CMC of the present invention can be directly used as an adsorbent or a liquid absorber. Of course, the CMC of the present invention can be applied to the field where the ion exchange property of CMC is utilized. Moreover, the product of the present invention can be widely used for medical materials, sanitary materials and industrial materials. Furthermore, CMC of the present invention in the form of a sheet, a woven fabric or a nonwoven fabric shows excellent processability when it is formed into a final product. In the case of conventional powdery CMC, in order to obtain, for example, a sanitary article, there should be adopted troublesome steps of appropriately arranging powdery CMC in a sheet composed of other material and sewing the sheet to a base fabric. Moreover, since CMC is in the powdery form, the inherent absorbing capacity is not completely exerted. In contrast, if CMC or its salt in the form of a sheet, a woven fabric or a nonwoven fabric according to one embodiment of the present invention is used for production of a sanitary article, the sanitary article can be made only by sewing of this CMC to a base fabric, and the absorbing capacity can be fully exerted. This CMC structure according to the present invention can be formed into a piled material with a sheet, woven fabric or nonwoven fabric composed of other material. Needless to say, the CMC of the present invention can be used in any form as one constituent of a structure.

The present invention will now be described in detail with reference to the following examples, which by no means limit the scope of the invention.

EXAMPLE 1

This example is given to illustrate that the difference of the structure among starting celluloses is likely to be retained after carboxymethylation and that the CMC of the present invention is excellent in the liquid or moisture absorbing property.

10 g of a cellulose fiber regenerated from a cuprammonium solution (crystal form of cellulose II, X-ray diffraction peaks at $2\theta = 9.5°$, 12.0°, 20.1° and 21.5°, crystallinity of 49.8%, degree of polymerization (DP) of 460) was immersed in 50 g of an aqueous solution containing sodium hydroxide in an amount of 1.34 moles per mole of the glucose residue at 30° C. The cellulose fiber was allowed to stand in this state for 20 minutes. Then, 6.4 g of isopropyl alcohol containing monochloroacetic acid in an amount of 0.56 mole per mole of the glucose residue was added. The temperature was elevated to 60° C., and the reaction was conducted for 90 minutes in the stationary state. After completion of the reaction, neutralization and washing were effected with a liquid mixture of methanol and hydrochloric acid. The <<F>> value of the thus obtained filamentary CMC was 0.34, and the <<f_6>>/(<<f_2>>+<<f_3>>) ratio was 1.8. In the X-ray diffraction pattern of this CMC, peaks were observed at $2\theta=9.5°$ and 20.1°. It was confirmed that there was a tendency of retaining the crystal form of cellulose II. This CMC was vacuum-dried and allowed to stand in an atmosphere maintained at a temperature of 18° C. and a relative humidity of 60%. Then, the weight of CMC was measured, and the CMC was dipped in pure water maintained at 37° C. for 10 minutes. Excessive water was removed by standing for 20 minutes and the weight was measured. It was found that CMC absorbed water in an amount 58 times its own weight.

For comparison, natural cellulose (crystal form of cellulose I, X-ray diffraction peaks at $2\theta=9°$, 14.7°, 16.4° and 22.6°, crystallinity of 50.4%, DP of 470) was treated and carboxymethylated under the same conditions as described above. The <<F>> value was 0.25, and the reaction efficiency of monochloroacetic acid was lower than in the above-mentioned example of the present invention. Furthermore, carboxymethylation was carried out in the same manner as described above except that sodium monochloroacetate was used instead of monochloroacetic acid and the amount of sodium monochloroacetate was increased to 0.70 mole per mole of the glucose residue. The <<F>> value was 0.33 and the <<f_6>>/(<<f_2>>+<<f_3>>) ratio was 1.1. Also this comparative CMC tended to retain the crystal form of cellulose I. The amount of water absorbed at 37° C. in this comparative CMC was only 45 times its own weight.

Figure 2:
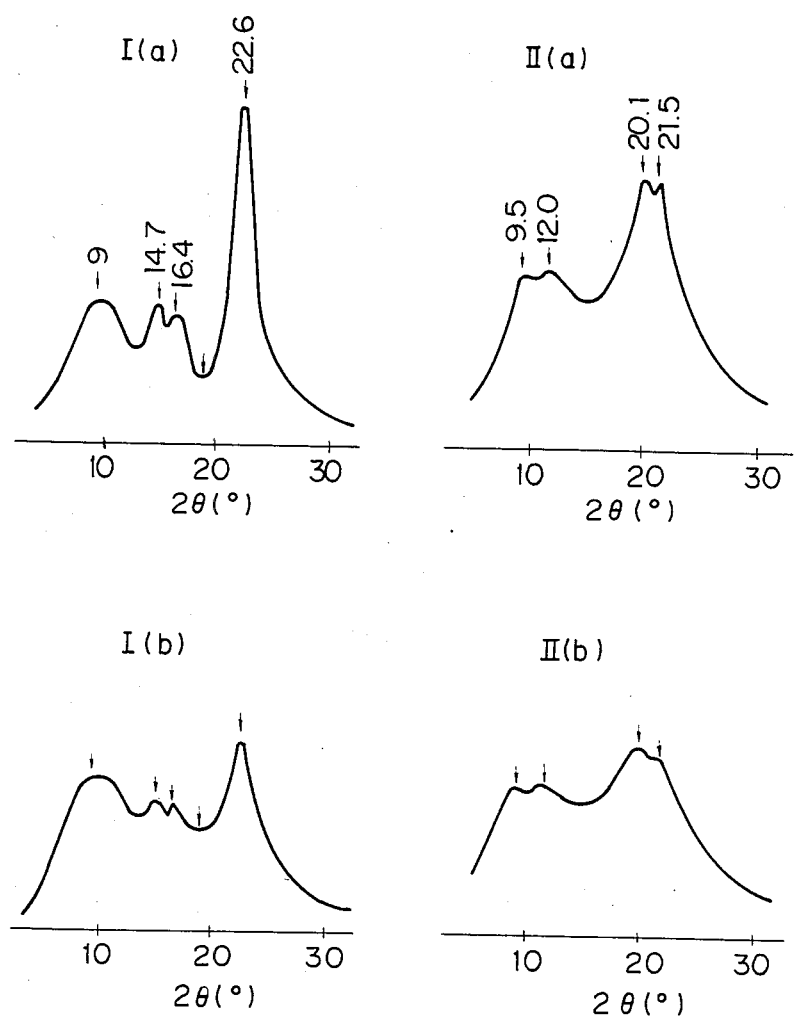
FIG. 2 shows X-ray diffraction patterns of the following celluloses and CMC's.

The <<F>> was measured according to the neutralizing titration method. The crystallinity was determined according to the method of L. Segal et al Text. Res. J., 10, 786 (1959). The X-ray diffraction diagrams of CMC of the present invention, comparative CMC and starting celluloses are shown in FIG. 2, in which I(a) shows the X-ray diffraction pattern of the starting cellulose of a crystal form of cellulose I, II(a) shows the X-ray diffraction pattern of the starting cellulose of a crystal form of cellulose II, I(b) shows the X-ray diffraction pattern of CMC obtained from the former starting cellulose and II(b) shows the X-ray diffraction pattern of CMC obtained from the latter starting cellulose.

EXAMPLE 2

This example is given to illustrate that CMC of the present invention having an <<F>> value of 0.10 to 0.64 is capable of absorbing water in an amount at least 20 times its own weight.

Nine kinds of CMC differing in the <<F>> within the range of from 0.09 to 0.75 were prepared according to the method described below by using regenerated cellulose having a DP of 400 and a crystallization degree of 46%, which was formed from viscose. Namely, 10 g of regenerated cellulose was immersed in 50 g of an aqueous solution of NaOH having a concentration of 5% by weight at 25° C. A predetermined amount of sodium monochloroacetate dissolved in isopropanol was added to the mixture and reaction was carried out at 60° C. for 90 minutes. After neutralization and drying, the amount of pure water absorbed at 37° C. was measured. The obtained results are shown in Table 2.

For comparison, natural cellulose (polymerization degree of about 350, crystallization of 41%) obtained by acid-hydrolyzing Polynier pulp customarily used for production of CMC and pulverizing the hydrolyzed cellulose by a ball mill was treated in the same manner as described above to obtain comparative CMC samples differing in the <<F>>. The amount of pure water absorbed at 37° C. was measured. The results are shown in Table 2.

The amount of absorbed pure water was determined according to the method described in Example 1, and the <<F>> value was determined according to the neutralizing titration method.

TABLE 2

| CMC of Present Invention | <<F>> | <<f_6>>/(<<f_2>> + <<f_3>>) | Amount of Absorbed Water (times) | Comparative CMC | <<F>> | <<f_6>>/(<<f_2>> + <<f_3>>) | Amount of Absorbed Water (times) |
|---|---|---|---|---|---|---|---|
| (a) | 0.09 | ∞ | 17.5 | (a) | 0.05 | 10.2 | 14.2 |
| (b) | 0.10 | 156 | 23.0 | (b) | 0.13 | 8.3 | 19.0 |
| (c) | 0.22 | 156 | 52.0 | (c) | 0.20 | 1.1 | 27.0 |
| (d) | 0.30 | 2.2 | 52.0 | (d) | 0.27 | 1.3 | 42.5 |
| (e) | 0.34 | 2.8 | 60.0 | (e) | 0.35 | 1.0 | 44.0 |
| (f) | 0.40 | 18 | 37.0 | (f) | 0.47 | 0.81 | 62.0 |
| (g) | 0.52 | 1.6 | 24.0 | (g) | 0.59 | 0.52 | 44.0 |
| (h) | 0.64 | 1.9 | 21.0 | (h) | 0.64 | 0.43 | 44.0 |
| (i) | 0.75 | 1.3 | 15.0 | | | | |

From the results shown in Table 2, it is seen that CMC of the present invention having a total substitution degree <<F>> of 0.10 to 0.64 has a high pure water absorbing property and the absorbing property is highest when the <<F>> value is about 0.22 to about 0.34. In case of comparative CMC, the highest absorbing property is obtained when the <<F>> value is 0.35 to 0.59. In short, CMC of the present invention is characterized in that the <<F>> value giving a highest absorbing property is smaller than in case of comparative CMC. Therefore, the stability of the gel after absorption of pure water in case of CMC of the present invention is much better than in case of comparative CMC.

EXAMPLE 3

This example is given to illustrate that CMC of the present invention satisfying the requirement of <<F_6>>/(<<F_2>>+<<F_3>>)≧1.5 absorbs a large amount of a physiological saline solution.

CMC of the present invention was prepared by treating 10 g of regenerated cellulose (the same as described in Example 1) prepared from a cuprammonium ammonium solution of cellulose with a reaction liquid having a composition shown in Table 3. In Table 3, "reaction liquid (a)" is a mixed solution of 38.2 ml of isopropanol, 22.4 ml of methanol and 12.8 ml of water containing 3.3 g of sodium hydroxide. This mixed solution was used for immersion of the cellulose at normal temperature for 20 minutes. Then, "reaction liquid (b)" was added to the mixture and carboxy-methylation was carried out at 60° C. for 90 minutes. In Table 3, "reaction liquid (b)" is a solution of 2.5 g of monochloroacetic acid in 6.6 ml of isopropanol. After the carboxymethylation, neutralization was carried out according to customary procedures by using a liquid mixture of methanol and water containing acetic acid, and formed CMC was washed with methanol.

For comparison, natural cellulose (DP of 400, crystallinity degree of 50.1%) was converted to CMC according to the same procedures as described above.

With respect to each of the CMC of the present invention and comparative CMC, the physiological saline solution absorbing property was evaluated. The results are shown in Table 4.

As described in Example 1, in order to prepare comparative CMC having an $<<F>>$ value equivalent to that of the CMC of the present invention, the amount of monochloroacetic acid used as the reactant had to be increased.

large, and this large $<<f_6>>$ value makes a great contribution to enhancement of the capacity of absorbing a physiological saline solution.

From X-ray diffractometry, it was confirmed that in the course of preparation of the CMC of the present invention, no/complete alkali cellulose is formed. The results are shown in FIG. 3. In FIG. 3, I($a$), II($a$), I($b$), and II($b$) show X-ray diffractometric diagrams of the following celluloses.

I($a$): Cell I + alkaline solvent, Cell I
II($a$): Cell II + alkaline solvent, Cell II
I($b$): Cell + 18% NaOH, Na-Cell I-I
II($b$): Cell II + 18% NaOH, Na-Cell I-II It is seen that CMC or its salt of the present invention is formed by carboxymethylation of cellulose treated with an alkaline solution in which X-ray diffraction peaks of the starting cellulose II at $2\theta = 10°$, $20°$ and $21°$ are retained. Characteristic peaks of ordinary alkali cellulose at $2\theta = 14°$ and $30°$ do not appear in this alkali-treated cellulose. This holds good when natural cellulose is treated by a method similar to the method of the present invention.

EXAMPLE 4

This example is given to illustrate that a CMC structure having a good processability and a good handling property can be obtained from regenerated cellulose in the form of a nonwoven fabric according to the present invention.

A nonwoven fabric of regenerated cuprammonium

TABLE 3

| | Conditions for Preparation of CMC II of Present Invention | | | | | | |
|---|---|---|---|---|---|---|---|
| CMC of Present Invention | Reaction Liquid (a) (g/10 g of cellulose) | Reaction Liquid (b) (g/10 g of cellulose) | $<<F>>*^1$ | Comparative CMC | Reaction Liquid (a) (g/10 g of cellulose) | Reaction Liquid (b) (g/10 g of cellulose) | $<<F>>*^1$ |
| (1) | 64*² | 2.1*³ | 0.09 | (1) | 64 | 7.1 | 0.20 |
| (2) | 64 | 5.7 | 0.20 | (2) | 64 | 8.6 | 0.35 |
| (3) | 64 | 8.6 | 0.39 | (3) | 192 | 25.5 | 0.59 |
| (4) | 192 | 19.8 | 0.52 | | | | |
| (5) | 192 | 25.5 | 0.64 | | | | |

Note
¹determined according to the neutralizing titration method
²the amount of NaOH corresponded to 1.34 moles per mole of the glucose residue
³the amount of monochloroacetic acid corresponding to 0.143 mole per mole of the glucose residue

TABLE 4

| | Distribution of Substitution Degree and Physiological Saline Solution Absorbing Property | | | |
|---|---|---|---|---|
| CMC | $<<F>>*^1$ | $<<F>>*^2$ | $<<f_6>>/(<<f_2>>/<<f_3>>)$ | Physiological Saline Solution Absorbing Property (times) |
| Present Invention | | | | |
| (1) | 0.09 | 0.03 | ∞ | 17.5 |
| (2) | 0.20 | 0.14 | 4.95 | 26.0 |
| (3) | 0.39 | 0.26 | 265 | 40.0 |
| (4) | 0.52 | 0.54 | 8.20 | 58.0 |
| (5) | 0.64 | 0.64 | 5.86 | 30.0 |
| Comparison | | | | |
| (1) | 0.20 | 0.23 | 0.50 | 22.0 |
| (2) | 0.35 | 0.40 | 1.10 | 19.0 |
| (3) | 0.59 | 0.59 | 0.52 | 29.0 |

Note
*¹determined according to the neutralizing titration method
*²determined by NMR The $<<F>>$ values determined by the two methods are different in the lower substituted products. It is believed that this difference is due to the Overhauser effect.

As is seen from the results shown in Table 4, the $<<f_6>>$ value of the CMC of the present invention is rayon filaments (Bemlease ® supplied by Asahi Kasei Kogyo K.K.) was cut into square pieces having a size of 10 cm x 10 cm. The cut pieces were piled so that the total amount became 10 g. A nonwoven CMC fabric having an $\langle\langle F\rangle\rangle$ value of 0.37 and an $\langle\langle f_6\rangle\rangle/(\langle\langle f_2\rangle\rangle+\langle\langle f_3\rangle\rangle)$ ratio of 1.89 was prepared from this piled fabric according to the method described in Example 3. This carboxymethylated nonwoven fabric could absorb a physiological saline solution in an amount 40 times its own weight. Furthermore, the nonwoven fabric could absorb artificial urine (urea/NaCl/MgSO$_4$/CaCl$_2$/H$_2$O weight ratio =1.94/0.8/0.11/0.26/97.09) in an amount 45 times its own weight and artificial blood (NaCl/Na$_2$CO$_3$/glycerol/Na -CMC/water weight ratio =1.0/0.4/10.0/0.46/88.14) in an amount 35.0 times its own weight. This CMC nonwoven fabric could easily be cut and sewn to other material and could easily be formed into a body fluid absorber.

EXAMPLE 5

To 10 g of CMC (e) of the present invention obtained in Example 2 was supplied water to highly swell the cellulose, and 30 g of Manila hemp was added to the swollen cellulose. Water was further added and the dispersion was sufficiently mixed and then cast on a paper-making net to remove water while methanol was added, whereby a filter product was obtained. This product was excellent in the wet strength over a filter product obtained by using CMC of the present invention alone, and the product had a very good shape-retaining property. The product could be used as a body fluid absorbing material, an ion exchange material and a water-removing material.

We claim:

1. Carboxymethyl cellulose or its salt derived from cellulose having a crystal form of cellulose wherein the total degree of substitution $\langle\langle F\rangle\rangle$ of the carboxymethyl cellulose or its salt represented by the following formula:

$$\langle\langle F\rangle\rangle=\langle\langle f_2\rangle\rangle+\langle\langle f_3\rangle\rangle+\langle\langle f_6\rangle\rangle$$

wherein $\langle\langle f_2\rangle\rangle$, $\langle\langle f_3\rangle\rangle$ and $\langle\langle f_6\rangle\rangle$ represent the probabilities of substitution of substituent groups for OH groups located at the C$_2$, C$_3$ and C$_6$ positions, respectively, of the glucose ring constituting the cellulose, is in the range of from 0.10 to 0.64 and the $\langle\langle f_6\rangle\rangle/(\langle\langle f_2\rangle\rangle+\langle\langle f_3\rangle\rangle)$ ratio is at least 1.5.

2. Carboxymethyl cellulose salt according to claim 1, which absorbs pure water at 37° C. in an amount at least 20 times its own weight.

3. Carboxymethyl cellulose salt according to claim 1, wherein the total degree of substitution $\langle\langle F\rangle\rangle$ is in the range of from 0.25 to 0.64 and the salt absorbs a physiological saline solution at 37° C. in an amount at least 25 times its own weight.

4. Carboxymethyl cellulose or its salt according to any one of the preceding claims, which is in the form of a sheet, a woven fabric or a nonwoven fabric.

5. A structure in the form of a sheet, a woven fabric or a nonwoven fabric, which comprises, as one constituent, carboxymethyl cellulose or its salt derived from cellulose having a crystal form of cellulose II, wherein the total degree of substitution $\langle\langle F\rangle\rangle$ of the carboxymethyl cellulose or its salt represented by the following formula:

$$\langle\langle F\rangle\rangle=\langle\langle f_2\rangle\rangle+\langle\langle f_3\rangle\rangle+\langle\langle f_6\rangle\rangle$$

wherein $\langle\langle f_2\rangle\rangle$, $\langle\langle f_3\rangle\rangle$ and $\langle\langle f_6\rangle\rangle$ represent the probabilities of substitution of substituent groups for OH groups located at the C$_2$, C$_3$ and C$_6$ positions, respectively, of the glucose ring constituting the cellulose, is in the range of from 0.10 to 0.64 and the $\langle\langle f_6\rangle\rangle/(\langle\langle f_2\rangle\rangle+\langle\langle f_3\rangle\rangle)$ ratio is at least 1.5.

6. A structure according to claim 5, which comprises, as one constituent, carboxymethyl cellulose capable of absorbing pure water at 3720 C. in an amount at least 20 times its own weight.

7. A structure according to claim 5, which comprises, as one constituent, carboxymethyl cellulose salt in which the total degree of substitution $\langle\langle F\rangle\rangle$ is 0.25 to 0.64 and which absorbs a physiological saline solution at 37° C. in an amount at least 25 times its own weight.

8. A structure according to claim 5, which is a piled material composed of carboxymethyl-cellulose or its salt in the form of a sheet, a woven fabric or a nonwoven fabric and other material in the form of a sheet, a woven fabric or a nonwoven fabric.

9. A process for the preparation of carboxymethyl cellulose or its salt in which the total degree of substitution $\langle\langle F\rangle\rangle$ represented by the following formula:

$$\langle\langle F\rangle\rangle=\langle\langle f_2\rangle\rangle+\langle\langle f_3\rangle\rangle+\langle\langle f_6\rangle\rangle$$

wherein $\langle\langle f_2\rangle\rangle$, $\langle\langle f_3\rangle\rangle$ and $\langle\langle f_6\rangle\rangle$ represent the probabilities of substitution of substituent groups for OH groups located at the C$_2$, C$_3$ and C$_6$ positions, respectively, of the glucose ring constituting the cellulose, is in the range of from 0.10 to 0.64 and the $\langle\langle f_6\rangle\rangle/(\langle\langle f_2\rangle\rangle+\langle\langle f_3\rangle\rangle)$ ratio is at least 1.5, said process comprising treating cellulose having a crystal form of cellulose II as the starting material with an alkali to such an extent that the cellulose is not X-ray-diffractometrically completely converted to alkali cellulose, and then reacting the treated cellulose with monochloroacetic acid or sodium monochloroacetate.

* * * * *